US 8,450,258 B2

United States Patent
Nguyen et al.

(10) Patent No.: US 8,450,258 B2
(45) Date of Patent: May 28, 2013

(54) COMPOSITIONS COMPRISING AT LEAST ONE SILICONE PHOSPHATE COMPOUND AND AT LEAST ONE AMINE COMPOUND, AND METHODS FOR USING THE SAME

(75) Inventors: Nghi Van Nguyen, Edison, NJ (US); Hitendra Mathur, Woodbridge, NJ (US); David W. Cannell, Plainfield, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/947,466

(22) Filed: Nov. 16, 2010

(65) Prior Publication Data

US 2011/0114109 A1      May 19, 2011

Related U.S. Application Data

(63) Continuation of application No. 10/259,741, filed on Sep. 30, 2002, now abandoned.

(51) Int. Cl.
*C11D 9/36* (2006.01)
*C11D 3/30* (2006.01)

(52) U.S. Cl.
USPC ........... 510/122; 510/119; 510/120; 510/466; 510/467; 510/499

(58) Field of Classification Search
USPC ................ 510/119, 120, 122, 466, 467, 499
See application file for complete search history.

(56) References Cited

U.S. PATENT DOCUMENTS

| 5,908,619 A * | 6/1999 | Scholz ........................ 424/78.02 |
| 2002/0004036 A1 * | 1/2002 | Piot et al. ...................... 424/70.7 |

* cited by examiner

*Primary Examiner* — Charles Boyer
(74) *Attorney, Agent, or Firm* — O'Brien Jones, PLLC

(57) ABSTRACT

Compositions, methods, and kits for caring for, treating, conditioning or durable conditioning of at least one keratinous fiber comprising at least one silicone compound comprising at least one phosphate group compound and at least one amine compound comprising greater than three amino groups, wherein the amino groups are identical or different.

46 Claims, No Drawings

COMPOSITIONS COMPRISING AT LEAST ONE SILICONE PHOSPHATE COMPOUND AND AT LEAST ONE AMINE COMPOUND, AND METHODS FOR USING THE SAME

This application is a continuation of application Ser. No. 10/259,741, filed Sep. 30, 2002 now abandoned, by inventors Nghi Van NGUYEN, Hitendra MATHUR and David W. CANNELL, entitled COMPOSITIONS COMPRISING AT LEAST ONE SILICONE PHOSPHATE COMPOUND AND AT LEAST ONE AMINE COMPOUND, AND METHODS FOR USING THE SAME, which is incorporated herein by reference.

The present invention relates to compositions, kits comprising these compositions, and methods for using these compositions for care, treatment, conditioning or durable conditioning of at least one keratinous fiber, including at least one human keratinous fiber, comprising at least one silicone compound comprising at least one phosphate group and at least one amine compound comprising greater than three amino groups, wherein the amino groups are identical or different.

Shampoos generally comprise surfactants, such as anionic surfactants, to clean the hair. It is known that anionic surfactants not only remove the dirt and soil but also remove the naturally-present sebum from hair. Thus, shampoos may leave the hair dull and dry, that is, with what is known in the art as "creak". This generally makes the hair extremely difficult to comb either wet or dry, and once dry, the hair may not be amenable to styling, and may have undesirable electrostatic properties, causing the hair to "fly away." Due to the unsatisfactory condition of shampooed hair, many consumers use a conditioning composition to improve at least one of these undesirable characteristics.

Conditioning agents include cationic compounds such as cationic surfactants and cationic polymers which may render the hair more manageable, at least temporarily. For example, quaternized ammonium compounds may be used as hair conditioning agents. These compounds may be substantive to the hair due to the ionic interaction between their positive charge on the ammonium nitrogen atom and negative charges on the surface of the hair fibers. This ionic interaction, in effect, allows the conditioning agents to coat the hair shaft and thereby prevent tangling and matting of the individual hair fibers. Thus, the ability of these cationic compounds to adsorb to and/or react with the keratinous material of the hair makes them desirable compounds for conditioning the hair, such as for detangling wet hair and imparting manageability to dry hair.

However, in some cases the effect of these conditioning agents may not be long lasting. Normally, because of the weak ionic bond between the quaternized ammonium compounds and the hair fiber, the quaternized ammonium compounds are washed off the hair easily. This is especially true during shampooing, wherein anionic surfactants are present, generally in high concentrations. In such a case, the anionic surfactants in the shampoo and the cationic conditioning agents are known to form a complex which may be easily removed from the hair during the shampooing and/or which decreases the cleansing capabilities of the anionic surfactant and the conditioning capabilities of the conditioning agent.

Further, certain silicone compounds have been used as conditioning agents. However, these compounds lack durability on the hair shaft as these compounds are generally hydrophobic. Accordingly, silicone compounds may not be deposited on the hair, or are easily removed due to their weak hydrophobic interactions with the keratinous material of the hair.

Accordingly, in practice, most consumers prefer to apply an anionic surfactant-based shampoo to cleanse the hair, then rinse the hair, follow rinsing by application of a conditioner composition including a conditioning agent, such as, for example, a cationic compound, to condition the hair, and then rinse the hair again. As discussed above, this may only lead to temporary conditioning of the hair, as the next shampoo may remove the majority of the conditioning agents from the hair. Thus, there is a need for compositions and methods that condition hair, such as, for example, that impart a durable conditioning to the hair.

Compositions containing certain silicone compounds, certain amine compounds and certain silicone compounds comprising an amino group have previously been disclosed. Certain phosphated silicone polymers are known. For example, U.S. Pat. Nos. 5,070,171 and 5,149,765, the disclosures of which are hereby incorporated herein by reference, relate to phosphated silicone polymers which are disclosed to provide a nonvolatile lubricant antistat which can be applied to a variety of fibers. Further for example, U.S. Pat. No. 5,093,452, the disclosure of which is hereby incorporated herein by reference, relates to silicone phosphate organic amine salts wherein one or more pendant phosphate groups in free acid form is/are neutralized with a fatty amine group. The organic amines may be chosen from alkyl amido amines, imidazoline, alkoxyethyl alkyl amines, and alkyl tertiary amines. However, these compounds may not impart durable conditioning to at least one keratinous fiber, and may not react to condition keratinous fibers in a synergistic manner.

Further for example, U.S. Pat. No. 5,362,484, the disclosure of which is hereby incorporated herein by reference, discloses a hair care composition for conditioning hair with silicone oil comprising a stable emulsion of water-insoluble hair conditioning silicone oil dispersed in a liquid carrier composed essentially of polyoxyalkylene glycol and an emulsifier consisting of a silicone phosphate salt in which the anionic moiety comprises a copolymer of dimethylpolysiloxane and polyoxyethylene.

In essence, certain silicone compounds and certain amine compounds have been applied to hair for numerous reasons from conditioning to cleansing. Clearly, however, not all silicone compounds are the same, nor are all amine compounds the same, and thus not all combinations of silicone compounds and amine compounds impart the same properties when applied to a keratinous fiber.

The inventors have envisaged the application to at least one keratinous fiber of at least one silicone compound comprising at least one phosphate group and at least one amine compound comprising greater than three amino groups, wherein the amino groups are identical or different. In particular, the inventors have discovered that such compositions, and methods comprising applying these compositions to at least one keratinous fiber condition the at least one keratinous fiber. The compositions of the invention may also be used to care for, or treat, the at least one keratinous fiber. Further, in one embodiment, the inventive compositions impart a durable conditioning to the at least one keratinous fiber.

Thus, to achieve at least one of these and other advantages, the present invention, in one aspect, provides a composition for conditioning at least one keratinous fiber comprising at least one silicone compound comprising at least one phosphate group and at least one amine compound comprising greater than three amino groups, wherein the amino groups may be identical or different, and further wherein the at least one silicone compound and the at least one amine compound are present in a combined amount effective to condition the at least one keratinous fiber. In one embodiment, the at least one silicone compound and the at least one amine compound are present in a combined amount effective to durably condition the at least one keratinous fiber. In one embodiment, the at least one silicone compound and the at least one amine compound are present in the inventive composition in a synergistically effective amount to condition at least one keratinous fiber.

In another embodiment, the present invention provides a composition for durable conditioning of at least one keratinous fiber comprising at least one silicone compound comprising at least one phosphate group and at least one amine compound comprising greater than three amino groups, wherein the amino groups may be identical or different, and further wherein the at least one silicone compound and the at least one amine compound are present in a combined amount effective to durably condition the at least one keratinous fiber. In one embodiment, the at least one silicone compound and the at least one amine compound are present in the inventive composition in a synergistically effective amount to durably condition at least one keratinous fiber.

In another embodiment, the present invention is drawn to a method for conditioning at least one keratinous fiber comprising applying to the at least one keratinous fiber comprising at least one silicone compound comprising at least one phosphate group and at least one amine compound comprising greater than three amino groups, wherein the amino groups may be identical or different, and further wherein the at least one silicone compound and the at least one amine compound are present in a combined amount effective to condition the at least one keratinous fiber. In one embodiment, the at least one silicone compound and the at least one amine compound are present in the inventive composition in a synergistically effective amount to condition at least one keratinous fiber. The at least one keratinous fiber may be rinsed after the application. The at least one keratinous fiber may be wet with water prior to application of the composition.

In another embodiment, the present invention is drawn to a method for durably conditioning at least one keratinous fiber comprising applying to the at least one keratinous fiber comprising at least one silicone compound comprising at least one phosphate group and at least one amine compound comprising greater than three amino groups, wherein the amino groups may be identical or different, and further wherein the at least one silicone compound and the at least one amine compound are present in a combined amount effective to durably condition the at least one keratinous fiber. In one embodiment, the at least one silicone compound and the at least one amine compound are present in the inventive composition in a synergistically effective amount to durably condition at least one keratinous fiber. The at least one keratinous fiber may be rinsed after the application. The at least one keratinous fiber may be wet with water prior to application of the composition.

In another embodiment, the present invention is drawn to a method for caring for or treating at least one keratinous fiber comprising applying to the at least one keratinous fiber at least one silicone compound comprising at least one phosphate group and at least one amine compound comprising greater than three amino groups, wherein the amino groups may be identical or different, and further wherein the at least one silicone compound and the at least one amine compound are present in a combined amount effective to condition the at least one keratinous fiber. In one embodiment, the at least one silicone compound and the at least one amine compound are present in the inventive composition in a synergistically effective amount to condition at least one keratinous fiber. The at least one keratinous fiber may be rinsed after the application. The at least one keratinous fiber may be wet with water prior to application of the composition.

In yet another embodiment, the present invention provides a kit for caring for, treating, conditioning, or durably conditioning comprising at least two compartments, wherein a first compartment comprises a first composition comprising at least one silicone compound comprising at least one phosphate group, and wherein a second compartment comprises a second composition comprising at least one amine compound comprising greater than three amino groups, wherein the amino groups are identical or different.

The present invention also provides compositions, kits comprising these compositions, and methods for using these compositions for care, treatment, conditioning or durable conditioning of at least one keratinous fiber, including at least one human keratinous fiber, comprising at least one silicone compound comprising at least one phosphate group and at least one compound chosen from at least one amine compound comprising greater than three amino groups as defined herein, silicone compounds comprising at least one amino group different from the at least one silicone compound comprising at least one phosphate group, aminosilicone compounds comprising at least one amino group wherein the aminosilicone compounds are different from the at least one silicone compound comprising at least one carboxylic acid group, aminated polysaccharides comprising at least one amino group, hydrolysates of aminated polysaccharides comprising at least one amino group, and aminated monosaccharides comprising at least one amino group, wherein the at least one silicone compound and the at least one compound are present in a combined amount effective to condition the at least one keratinous fiber.

Certain terms used herein are defined below:

"Amino groups" as defined herein includes primary amino groups, secondary amino groups, and tertiary amino groups, and further includes amino groups which are terminal, pendant, and intercalated in a skeleton of the at least one amine compound, but does not, for example, include quaternary amino groups, amido groups, imino groups, nitrilo groups, or heteroatom analogs of any of the foregoing.

"At least one" as used herein means one or more and thus includes individual components as well as mixtures/combinations.

"Conditioning" as used herein means imparting to at least one keratinous fiber at least one property chosen from combability, manageability, moisture-retentivity, luster, shine, and softness. The state of conditioning is evaluated by measuring, and comparing, the ease of combability of the treated hair and of the untreated hair in terms of combing work (gm-in). See Examples 1-8.

"Formed from," as used herein, means obtained from chemical reaction of, wherein "chemical reaction," includes spontaneous chemical reactions and induced chemical reactions. As used herein, the phrase "formed from", is open ended and does not limit the components of the composition to those listed, e.g., as component (i) and component (ii). Furthermore, the phrase "formed from" does not limit the order of adding components to the composition or require that the listed components (e.g., components (i) and (ii)) be added to the composition before any other components.

"Durable conditioning" as used herein, means that, following at least six shampoos after treatment, treated hair remains in a more conditioned state as compared to untreated hair.

"Hydrocarbons," as used herein, include alkanes, alkenes, and alkynes, wherein the alkanes comprise at least one carbon, and the alkenes and alkynes each comprise at least two carbons; further wherein the hydrocarbons may be chosen from linear hydrocarbons, branched hydrocarbons, and cyclic hydrocarbons; further wherein the hydrocarbons may optionally be substituted; and further wherein the hydrocarbons may optionally further comprise at least one heteroatom intercalated in the hydrocarbon chain, wherein the at least one heteroatom is different from the greater than three amino groups.

"Silicone compound," as used herein, includes, for example, silica, silanes, silazanes, siloxanes, and organosiloxanes; and refers to a compound comprising at least one silicon; wherein the silicone compound may be chosen from linear silicone compounds, branched silicone compounds, and cyclic silicone compounds; further wherein the silicone compound may optionally be substituted; and further wherein the silicone compound may optionally further comprise at least one heteroatom intercalated in the silicone chain, wherein the at least one heteroatom is different from the at least one silicon.

"Substituted," as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Ethylene oxide group" as defined herein refers to a group of formula —CH$_2$CH$_2$—O—.

"Propylene oxide group" as defined herein includes groups of formula —CH$_2$CH$_2$CH$_2$—O—, groups of formula (CH$_3$)CHCH$_2$—O—, and groups of formula —CH$_2$(CH$_3$)CH—O—.

"Keratinous fiber" as defined herein may be human keratinous fiber, and may be chosen from, for example, hair, eyelashes, and eyebrows.

"Polymers," as defined herein, include homopolymers and copolymers formed from at least two different types of monomers.

"Synergy," as used herein, refers to the phenomenon in which the effect of at least two components (e.g., the at least one silicone compound comprising at least one phosphate group and the at least one amine compound comprising at least three amino groups) is more than additive, i.e., the effect observed with the at least two components is greater than that observed for either component alone.

It is to be understood that both the foregoing general description and the following detailed description are exemplary and explanatory only and are not restrictive of the invention, as claimed. Reference will now be made in detail to exemplary embodiments of the present invention.

As described above, certain silicone compounds and certain amine compounds have been used in hair care compositions and other treatments for their detergency, surfactant and/or conditioning effect. However, it was unexpectedly discovered by the present inventors that a composition comprising at least one silicone compound chosen from a certain class of silicone compounds and at least one amine compound chosen from a certain class of amine compounds had at least one property that make it particularly desirable for use on keratinous fibers. For example, with respect to hair, compositions comprising at least one silicone compound comprising at least one phosphate group and at least one amine compound comprising greater than three amino groups (which amino groups may be identical or different) were found to condition the hair and also found to be useful in caring for and treating the hair. Further, these compositions may impart to the at least one keratinous fiber a durable conditioning even after shampooing the at least one keratinous fiber subsequent to treatment with such a composition.

Thus, in one embodiment, the present invention provides compositions for conditioning of at least one keratinous fiber comprising at least one silicone compound comprising at least one phosphate group and at least one amine compound comprising greater than three amino groups, wherein the amino groups may be identical or different, and further wherein the at least one silicone compound and the at least one amine compound are present in a combined amount effective to condition the at least one keratinous fiber.

According to the present invention, in some cases, the ratio of amino groups in the at least one amine compound to phosphate groups in the at least one silicone compound may not be determinative of the effectiveness of the inventive composition in conditioning at least one keratinous fiber as long as the at least one amine compound comprises greater than three amino groups. For example, the examples below show that the molecular weight, the concentration, and/or the nature of the silicone compound may affect the effectiveness of the composition comprising at least one silicone compound and the at least one amine compound in conditioning at least one keratinous fiber.

According to the present invention, the at least one silicone compound comprising at least one phosphate group may be chosen from water-soluble silicone compounds comprising at least one phosphate group, oil soluble silicone compounds comprising at least one phosphate group, water-dispersible silicone compounds comprising at least one phosphate group, and silicone compounds comprising at least one phosphate group which are soluble in organic solvents.

In one embodiment, the at least one silicone compound comprising at least one phosphate group further comprises at least one alkoxylated chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups ("EO"=—CH$_2$—CH$_2$—O—) and propylene oxide groups ("PO"=C$_3$H$_6$O).

The at least one phosphate group may be chosen from terminal phosphate groups and pendant phosphate groups. Further, the at least one phosphate group may be chosen from groups of formula —O—P(O)(OH)$_2$, groups of formula —O—P(O)(OH)(OR), and groups of formula —O—P(O)(OR)$_2$, wherein R may be chosen from H, inorganic cations, and organic cations. Non-limiting examples of inorganic cations include alkali metals, such as, for example, potassium lithium, and sodium. A non-limiting example of organic cations is at least one additional silicone compound which may be identical to or different from the at least one silicone compound bonded to the other oxygen of the phosphate group.

In one embodiment, the at least one silicone compound comprising at least one phosphate group is chosen from silicone compounds of formula (I):

(I)

wherein R¹, which may be identical or different, are each chosen from H, organic cations, inorganic cations, optionally substituted hydrocarbons (such as alkyl groups and alkenyl groups comprising from 1 to 22 carbon atoms), optionally substituted aromatic groups,
groups of formula (II) and salts thereof:

$$CH_3(CH_2)_x\text{—}O\text{-}(EO)_c\text{—}(PO)_d\text{-}(EO)_e\text{—}CH_2CH_2\text{—} \quad (II)$$

wherein:
   c, and d, which may be identical or different, are each integers ranging from 0 to 20;
   e is an integer ranging from 0 to 19; and
   x is an integer ranging from 0 to 21;
groups of formula (III) and salts thereof:

$$HO\text{-}(EO)_c\text{—}(PO)_d\text{-}(EO)_e\text{—}(CH_2)_x\text{—} \quad (III)$$

wherein:
   c, d, and e, which may be identical or different, are each integers ranging from 0 to 20; and
   x is an integer ranging from 0 to 21; and
groups of formula (IV) and salts thereof:

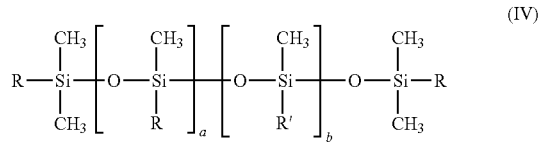

wherein:
   a is an integer ranging from 0 to 200;
   b is an integer ranging from 0 to 200;
   R', which may be identical or different, are each chosen from optionally substituted hydrocarbons, such as alkyl groups and alkenyl groups comprising from 1 to 22 carbon atoms, optionally substituted aromatic groups, groups of formula (III) as defined above and salts thereof; and
   R, which may be identical or different, are each chosen from optionally substituted hydrocarbons, such as alkyl groups and alkenyl groups comprising from 1 to 22 carbon atoms, optionally substituted aromatic groups, optionally substituted divalent hydrocarbons, such as alkylene groups and alkenylene groups comprising from 1 to 22 carbon atoms, optionally substituted divalent aromatic groups, groups of formula (III) as defined above and salts thereof, and groups of formula (V):

$$\text{-}(EO)_c\text{—}(PO)_d\text{-}(EO)_e\text{—}(CH_2)_3\text{—} \quad (V)$$

wherein:
   the $(CH_2)_3$ end is bonded to the silicon of the compound of formula (IV) and the (EO) or (PO) end, if present, is bonded to the oxygen of the compound of formula (I);
   c, d, and e, which may be identical or different, are each integers ranging from 0 to 20;
   EO is an ethylene oxide group; and
   PO is a propylene oxide group; and
   with the proviso that at least one R is chosen from groups of formula (V) and salts thereof; and
   with the further proviso that at least one R¹ is chosen from groups of formula (IV) and salts thereof and at least one other R¹ is chosen from H, organic cations, and inorganic cations.
Non-limiting examples of the inorganic cations include alkali metals, such as potassium, lithium, and sodium. Non-limiting examples of the at least one silicone compound include those commercially available from Phoenix Chemical, Inc. of New Jersey under the name of Pecosil®, such as Pecosil® PS-100, Pecosil® PS-112, Pecosil® PS-150, Pecosil® PS-200, Pecosil® WDS-100, Pecosil® WDS-200, Pecosil® PS-100 B, and Pecosil® PS-100 K and those commercially available from Siltech under the name Silphos A-100 and Silphos A-150. Other non-limiting examples of the at least one silicone compound include those described in U.S. Pat. Nos. 5,070,171, 5,093,452, and 5,149,765 the disclosures of which are incorporated herein by reference.

In one embodiment, the at least one silicone compound is present in the inventive composition in an amount ranging from 0.01% to 50% by weight relative to the total weight of the composition. In another embodiment, the at least one silicone compound is present in an amount ranging from 0.1% to 30% by weight relative to the total weight of the composition. One of ordinary skill in the art will recognize that the at least one silicone compound according to the present invention may be commercially available, and may come from suppliers in the form of a dilute solution. The amounts of the at least one silicone compound disclosed herein therefore reflect the weight percent of active material.

As previously defined, the greater than three amino groups of the at least one amine compound are chosen from primary amino groups, secondary amino groups and tertiary amino groups. In one embodiment, the greater than three amino groups are identical. In another embodiment, the greater than three amino groups are different.

The at least one amine compound of the present invention comprises greater than three amino groups. In one embodiment, the at least one amine compound of the present invention comprises at least four amino groups, such as greater than four amino groups. In one embodiment, the at least one amine compound of the present invention comprises at least five amino groups, such as greater than five amino groups. In one embodiment, the at least one amine compound of the present invention comprises at least six amino groups, such as greater than six amino groups. In one embodiment, the at least one amine compound of the present invention comprises at least ten amino groups, such as greater than ten amino groups.

The at least one amine compound may, for example, be chosen from hydrocarbons comprising greater than three amino groups, and silicone compounds comprising greater than three amino groups different from the at least one silicone compound comprising at least one phosphate group. In one embodiment of the present invention, the at least one amine compound may, for example, be chosen from aminosilicone compounds comprising at least three amino groups wherein the aminosilicone compounds are different from the at least one silicone compound comprising at least one carboxylic acid group. Non-limiting examples of suitable aminosilicone compounds comprising at least three amino groups are DC 2-8566 and DC 2-8902, both of which are commercially available from Dow Corning. In one embodiment of the present invention, the at least one amine compound may, for example, be chosen from aminated polysaccharides comprising greater than three amino groups, such as, for example, chitosan, and hydrolysates of aminated polysaccharides comprising greater than three amino groups. In one embodiment, the at least one amine compound may, for example, be chosen from polymers. Suitable polymers for use as the at least one amine compound are polymers comprising greater than three amino groups as defined herein. Non-limiting examples of suitable polymers include homopolymers comprising greater than three amino groups, copolymers comprising greater than three amino groups, and terpolymers comprising greater than three amino groups. Thus, the at least one amine compound comprising greater than three amino groups may be chosen from, for example, polymers comprising greater than three amino groups formed from (i) at least one monomer unit comprising greater than three amino groups as defined herein, and, optionally, (ii) at least one additional monomer unit different from the at least one monomer (i); and polymers comprising greater than three amino groups formed from (i) at least one monomer comprising at least one amino group as defined herein, and, optionally, (ii) at least one additional monomer unit different from the at least one monomer (i). According to the present invention, the at least one additional monomer different from the at least one monomer (i) may or may not comprise at least one amino group as defined herein.

In one embodiment of the present invention, the at least one amine compound is chosen from polyamines. As used herein, "polyamines" comprise at least two repeating units, wherein each unit comprises at least one amino group as defined herein. In one embodiment, polyamines are chosen from polyethyleneimines. Polyethyleneimines suitable for use in the compositions of the present invention may optionally be substituted. Non-limiting examples of polyethyleneimines which may be used in the composition according to the present invention are the Lupasol™ products commercially available from BASF. Suitable examples of Lupasol™ polyethyleneimines include Lupasol™ PS, Lupasol PL, Lupasol™ PR8515, Lupasol™ G20, Lupasol G35 as well as Lupasol™ SC® Polythyleneimine Reaction Products (such as Lupasol™ SC-61B®, Lupasol™ SC-62J®, and Lupasol™ SC-86X®). Other non-limiting examples of polyethyleneimines which may be used in the composition according to the present invention are the Epomin™ products commercially available from Aceto. Suitable examples of Epomin™ polyethyleneimines include Epomin™ SP-006, Epomin™ SP-012, Epomin™ SP-018, and Epomin™ P-1000.

In another embodiment, the at least one amine compound comprising greater than three amino groups is chosen from proteins and protein derivatives. Non-limiting examples of suitable proteins and protein derivatives for use in the present invention include those listed at pages 1701 to 1703 of the C.T.F.A. International Cosmetic Ingredient Dictionary and Handbook, 8$^{th}$ edition, vol. 2, (2000). In one embodiment, the at least one amine compound comprising greater than three amino groups is chosen from wheat protein, soy protein, oat protein, collagen, and keratin protein.

In one embodiment, the at least one amine compound comprising greater than three amino groups is not chosen from proteins and protein derivatives. In one embodiment, the at least one amine compound comprising greater than three amino groups is not chosen from compounds comprising lysine, compounds comprising arginine, and compounds comprising histidine. In one embodiment, the at least one amine compound comprising greater than three amino groups is chosen from compounds comprising lysine, compounds comprising arginine, compounds comprising histidine, and compounds comprising hydroxylysine.

In one embodiment, the at least one amine compound is present in the inventive composition in an amount ranging from 0.01% to 30% by weight relative to the total weight of the composition. In another embodiment, the at least one amine compound is present in an amount ranging from 0.1% to 15% by weight relative to the total weight of the composition. One of ordinary skill in the art will recognize that the at least one amine compound according to the present invention may be commercially available, and may come from suppliers in the form of a dilute solution. The amounts of the at least one amine compound disclosed herein therefore reflect the weight percent of active material.

In one embodiment of the present invention, the at least one silicone compound and the at least one amine compound are present in the inventive composition in a synergistically effective amount to condition at least one keratinous fiber. Example 1 provides for a simple screening test, the combability test (See Garcia, M. L., and Diaz, J., J. Soc. Cosmet. Chem. 27, 370-398 (1976)), to determine the presence of synergy and what constitutes a synergistically effective amount of the at least one silicone compound and the at least one amine compound in such mixtures. The combability test is known in the art to correlate well to the amount of conditioning that is afforded hair by a composition. Wet combing work of normal hair is determined prior to treatment. The hair is then divided into three groups and treated, one group with a composition comprising both the at least one silicone compound and the at least one amine compound, a second group with a control solution containing the at least one silicone compound alone, and a third group with a control solution containing the at least one amine compound alone. The increase in work or force required to comb wet hair is compared for hair treated with the inventive composition versus the hair treated with the controls to determine if a synergistic effect is observed.

The compositions of the present invention as well as those used in the methods of the present invention may, for example, be in the form of a shampoo, a conditioner, a hair dye, a hair bleach, a permanent waving product, a relaxing product, a styling product, or a hair care product, such as a hair treatment. The inventive compositions may further comprise at least one solvent. Non-limiting examples of the at least one solvent include water and organic solvents. Non-limiting examples of organic solvents include $C_1$-$C_4$ alkanols, such as ethanol and isopropanol; glycerol; glycols and glycol ethers, such as 2-butoxyethanol, propylene glycol, propylene glycol monomethyl ether, diethylene glycol monoethyl and monomethyl ether, and aromatic alcohols, such as benzyl alcohol and phenoxyethanol, and mixtures thereof. Further, the inventive compositions may be acidic or basic.

In one embodiment, these compositions may further comprise at least one suitable additive chosen from additives commonly used in compositions for keratinous fibers. Non-limiting examples of the at least one suitable additive include anionic surfactants different from the at least one silicone compound and from the at least one amine compound, cationic surfactants different from the at least one silicone compound and from the at least one amine compound, nonionic surfactants different from the at least one silicone compound and from the at least one amine compound, amphoteric surfactants different from the at least one silicone compound and from the at least one amine compound, zwitterionic surfactants different from the at least one silicone compound and from the at least one amine compound, thiol compounds, fragrances, penetrating agents, antioxidants, sequestering agents, opacifying agents, solubilizing agents, emollients, colorants, screening agents (such as sunscreens and UV filters), preserving agents, vitamins, silicones, polymers such as thickening polymers different from the at least one silicone compound and from the at least one amine compound, plant oils, mineral oils, synthetic oils and any other additive conventionally used in compositions for the conditioning, care and/or treatment of at least one keratinous fiber.

Needless to say, a person skilled in the art will take care to select the at least one suitable additive such that the advantageous properties of the composition in accordance with the invention are not, or are not substantially, adversely affected by the addition(s) envisaged.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific example are reported as precisely as possible. Any numerical value, however, inherently contains certain errors necessarily resulting from the standard deviation found in their respective testing measurements. The following example is intended to illustrate the invention without limiting the scope as a result.

EXAMPLES

Example 1

The Synergistic Effects of a Composition Comprising at Least One Silicone Compound and at Least One Amine Compound A solution containing a combined amount of 5% by weight of Pecosil® PS-100 (3.92% by weight) and Lupasol™ PR8515 (1.08% by weight) and having a pH adjusted to 6 was used to treat bleached hair swatches (0.5 g of solution/g hair). After 2 minutes of treatment, the hair swatches were rinsed with warm water for 1 minute. Before and after treatment, the force needed to comb through the wet hair swatches was determined using an Instron Tensile Tester. After the initial treatment and combability test, the hair swatches were shampooed 6 times with 10% SLES, and the combability of the shampooed hair swatches was determined. The percent improvement (% improvement) is defined as:

% Improvement=$(W_b-W_a)/W_b \times 100$% where $W_b$=Combing Work before treatment
$W_a$=Combing Work after treatment, or Combing Work after 6 shampoos following treatment The same procedure was repeated with hair swatches that were treated with a solution containing Pecosil® PS-100 (7.84% by weight) and hair swatches that were treated with a solution containing Lupasol PR8515 (2.16% by weight relative to the total weight of the composition). All results are the average of duplicate experiments. Table 1 shows the % improvement of the combability of hair swatches after the treatment.

TABLE 1

Synergy of at least one silicone compound and at least one amine compound

| Rinse-off Treatment | % Improvement After Treatment | % Improvement After 6 Shampoos |
|---|---|---|
| Polyethyleneimine Solution (2.16%) | 38.81 | −10.17 |
| Silicone Compound Solution (7.84%) | 14.00 | −196.85 |
| Silicone Compound/ | 71.59 | 62.54 |

TABLE 1-continued

Synergy of at least one silicone compound and at least one amine compound

| Rinse-off Treatment | % Improvement After Treatment | % Improvement After 6 Shampoos |
|---|---|---|
| Polyethyleneimine Solution (5%: 3.92% Silicone; 1.08% PEI) | | |

The data show that the % Improvement in wet combability of hair treated with the solution containing both the silicone compound and the amine compound is much greater than the % Improvement in wet combability of hair treated with either a solution containing only polyethyleneimine or solution containing only a silicone compound solution, despite the higher concentration of silicone compound and PEI in the latter. Thus, the inventive composition containing both at least one silicone compound and the at least one amine compound exhibits a synergistic effect compared to compositions comprising only one of its individual components.

Example 2

Durable Conditioning Effects of the Silicone Compound/Amine Compound Composition Following the procedure of Example 1, bleached hair swatches were treated with a solution containing a silicone compound/amine compound composition in a combined amount of 7% by weight relative to the total weight of the composition formed from Pecosil PS-100 (5.81% by weight) and Lupasol G-35 (1.19% by weight). After the initial treatment and combing test, the wet combability test was also performed after the hair swatches were shampooed 6 times with 10% SLES. The results are shown in Table 2.

TABLE 2

Durable Conditioning Effects of the Silicone Compound/Amine Compound Composition

| Rinse-off Treatment | % Improvement After Treatment | % Improvement After 6 Shampoos |
|---|---|---|
| Silicone/Amine Composition | 62.36 | 38.32 |

The results indicate that even after 6 shampoos the hair treated with the silicone/amine composition was still conditioned.

Example 3

Effects of the Molecular Weight of the Silicone Compound on the Durability of the Conditioning by the Composition Following the procedure in Example 2, bleached hair swatches were treated with a series of solutions containing a silicone compound and an amine compound in a combined amount of 5% by weight relative to the total weight of the composition. The silicone compounds in the silicone compound/amine compound composition were Pecosil® PS-100 (low molecular weight silicone phosphate) and Pecosil® PS-200 (high molecular weight silicone phosphate). The amine compound was Lupasol G-35. All solutions had a 1:5 ratio of the acid number of the silicone compound to the amine number of the amine compound. The results from the wet combability tests are shown in Table 3.

TABLE 3

Effects of the Molecular Weight of the Silicone Compound

| Silicone Compound | % Improvement After Treatment | % Improvement After 6 Shampoos |
|---|---|---|
| Pecosil ® PS-100 | 51.83 | 15.47 |
| Pecosil ® PS-200 | 64.99 | 70.38 |

The results indicate that the durable conditioning effects of the silicone compound/amine compound composition increased as did the molecular weight of the silicone compound.

Example 4

Effects of the Concentration of the Silicone Compound/Amine Compound Composition on the Durable Conditioning Following the procedure in Example 2, bleached hair swatches were treated with solutions containing both a silicone compound and an amine compound in a combined amount of 2% by weight (1.57% by weight Pecosil® PS-100, 0.43% Lupasol PR8515) and 5% by weight (3.92% by weight Pecosil® PS-100, 1.08% Lupasol PR8515) relative to the total weight of the composition. The results from the wet combability tests are shown in Table 4.

TABLE 4

Effects of the Concentration of the Silicone Compound/Amine Compound Composition

| Concentration of Solution (%) | % Improvement After Treatment | % Improvement After 6 Shampoos |
|---|---|---|
| 2 | 71.40 | 20.32 |
| 5 | 71.59 | 62.54 |

The results indicate that durable conditioning of hair is possible with a solution comprising 2% of the silicone compound/amine compound composition. Further, the results indicate that the durable conditioning effect increased as did the concentration of the at least one silicone compound and the at least one amine compound.

Examples 5, 6 and 7

The following examples illustrate the use of the inventive compositions for conditioning at least one keratinous fiber in various surfactant systems (anionic, nonionic and amphoteric surfactants). The effectiveness of the inventive composition on hair was determined by the % Improvement as defined in Example 1.

Example 5

Durable Conditioning Effects of the Silicone Compound/Amine Compound Composition in Various Surfactant Systems at Acidic pH Following the procedure in Example 1, bleached hair swatches were treated with one of three solutions containing both a silicone compound and an amine compound in a combined amount of 3% by weight relative to the total weight of the composition formed from 2.32% by weight Pecosil® PS-100 and 0.68% Lupasol G-35 at pH 5. The anionic surfactant system consisted of the silicone compound and the amine compound in a combined amount of 3% and 8.8% trideceth-7 carboxylic acid (Surfine T-A commercially available from FineTex). The amphoteric surfactant system consisted of the silicone compound and the amine compound in a combined amount of 3% and 6% disodium cocoamphodipropionate (Mackam 2CSF40 CG commercially available from McIntyre). The nonionic surfactant system consisted of the silicone compound and the amine compound in a combined amount of 3%, 4% glyceryl stearate and PEG-100 (Arlacel 165 FI commercially available from Uniquema), and 4% cetearyl alcohol (Lanetter O commercially available from Cognis). The results from the wet combability tests are shown in Table 5.

TABLE 5

Durable Conditioning Effects of the Silicone Compound/Amine Compound Composition in Various Surfactant Systems at pH 5

| Surfactant System | % Improvement After Treatment | % Improvement After 6 Shampoos |
|---|---|---|
| Anionic | 88.19 | 76.99 |
| Amphoteric | 76.82 | 67.41 |
| Nonionic | 82.07 | 68.54 |

The results indicate that durable conditioning of hair is achieved. Even after multiple shampoos, the hair treated with solutions containing the at least one silicone compound and the at least one amine compound in an anionic surfactant system, in an amphoteric surfactant system or in a nonionic-surfactant system at low pH remain conditioned.

Example 6

Durable Conditioning Effects of the Silicone Compound/Amine Compound Composition in Various Surfactant Systems at Basic pH Following the procedure in Example 1, bleached hair swatches were treated with one of three solutions containing both a silicone compound and an amine compound in a combined amount of 3% by weight relative to the total weight of the composition formed from 2.32% by weight Pecosil® PS-100 and 0.68% Lupasol G-35. The anionic surfactant system consisted of the silicone compound and the amine compound in a combined amount of 3% and 8.8% trideceth-7 carboxylic acid (Surfine T-A commercially available from FineTex) at pH 8. The amphoteric surfactant system consisted of the silicone compound and the amine compound in a combined amount of 3% and 6% disodium cocoamphodipropionate (Mackam 2CSF40 CG commercially available from McIntyre) at pH 10.5. The nonionic surfactant system consisted of the silicone compound and the amine compound in a combined amount of 3%, 4% glyceryl stearate and PEG-100 (Arlacel 165 FI commercially available from Uniquema), and 4% cetearyl alcohol (Lanetter O commercially available from Cognis) at pH 10.5. The results from the wet combability tests are shown in Table 6.

TABLE 6

Durable Conditioning Effects of the Silicone Compound/Amine Compound Composition in Various Surfactant Systems at High pH

| Surfactant System | % Improvement After Treatment | % Improvement After 6 Shampoos |
|---|---|---|
| Anionic | 86.08 | 72.98 |
| Amphoteric | 92.00 | 73.99 |
| Nonionic | 87.25 | 80.12 |

The results indicate that durable conditioning of hair is achieved. Even after multiple shampoos, the hair treated with solutions containing the at least one silicone compound and the at least one amine compound in an anionic surfactant system, in an amphoteric surfactant system or in a nonionic surfactant system at high pH remain conditioned.

Example 7

Durable Conditioning Effects of the Silicone Compound/Amine Compound Composition in Shampoos Following the procedure in Example 2, bleached hair swatches were treated with one of two shampoo-based solutions containing both a silicone compound (Pecosil® PS-100) and an amine compound (Lupasol G-35) and an amphoteric surfactant (either a sulfate compound or a carboxylate compound). The sulfate-containing shampoo contained the silicone compound and the amine compound in a combined amount of 3% by weight relative to the total weight of the composition formed from 2.32% Pecosil® PS-100 and 0.68% Lupasol G-35, 10% sodium laryl ether sulfate and 6% disodium cocoamphodipropionate at pH 5.5. The carboxylate-containing shampoo contained the silicone compound and the amine compound in a combined amount of 1% by weight relative to the total weight of the composition formed from 0.78% Pecosil® PS-100 and 0.22% Lupasol G-35, 4% trideceth-7 carboxylic acid, and 7.7% disodium cocoamphodipropionate at pH 5.5. The results from the wet combability tests are shown in Table 7.

TABLE 7

Durable Conditioning Effects of the Silicone Compound/Amine Compound Composition in Shampoo Systems

| Shampoo System | % Improvement After Treatment | % Improvement After 6 Shampoos |
|---|---|---|
| Sulfate/Amphoteric | 78.21 | 43.21 |
| Carboxylate/Amphoteric | 89.43 | 59.18 |

The results indicate that durable conditioning of hair is achieved. Even after multiple shampoos, the hair treated with shampoo-based solutions containing both the silicone compound and the amine compound in a sulfate/amphoteric surfactant system and a carboxylate/amphoteric surfactant system remain conditioned.

Example 8

Durable Conditioning Effects of the Silicone Compound/Amine Compound Composition in Conditioner Systems Following the procedure in Example 2, bleached hair swatches were treated with one of two conditioner-based solutions containing (1) either a silicone compound and an amine compound in a combined amount of 0.5% by weight (0.39% by weight Pecosil® PS-100 and 0.11% Lupasol G-35) or a silicone compound and an amine compound in a combined amount of 1% by weight (0.78% by weight Pecosil® PS-100 and 0.22% Lupasol G-35), (2) 4% glyceryl stearate and PEG-100 stearate, and (3) 4% cetearyl alcohol at pH 5.5. The results from the wet combability tests are shown in Table 8.

TABLE 8

Durable Conditioning Effects of the Silicone Compound/Amine Compound Composition in Conditioner Systems

| Combined Concentration of silicone compound and amine compound (%) | % Improvement After Treatment | % Improvement After 6 Shampoos |
|---|---|---|
| 0.5 | 80.93 | 79.05 |
| 1 | 90.39 | 76.85 |

The results indicate that durable conditioning of hair is achieved. Even after multiple shampoos, the hair treated with conditioner-based solutions containing both a silicone compound and an amine compound remained conditioned.

What is claimed is:

1. A composition for conditioning and/or durably conditioning at least one keratinous fiber comprising:
   (a) at least one silicone compound comprising at least one phosphate group; and
   (b) at least one amine compound comprising greater than three amino groups selected from the group consisting of aminated polysaccharides and polyethyleneimines;
   wherein said greater than three amino groups are identical or different;
   wherein the state of conditioning is evaluated by measuring, and comparing, the ease of combability of the treated hair and of the untreated hair in terms of combing work;
   wherein said at least one silicone compound and said at least one amine compound are present in a combined amount effective to condition the at least one keratinous fiber;
   wherein the ratio of the acid groups of the at least one silicone compound to the amine groups of the at least one amine compound ranges from about 1:2 to about 1:6; and
   further wherein the at least one keratinous fiber is human hair;
   provided that the composition does not comprise a sunscreen agent.

2. A composition according to claim 1, wherein said at least one silicone compound and said at least one amino compound are present in said composition in a synergistically effective amount to condition the at least one keratinous fiber.

3. A composition according to claim 1, wherein said at least one silicone compound and said at least one amine compound are present in a combined amount effective to durably condition said at least one keratinous fiber.

4. A composition according to claim 1, wherein said at least one silicone comprising at least one phosphate group further comprises at least one alkoxy group.

5. A composition according to claim 4, wherein said at least one alkoxy group is chosen from ethylene oxide groups and propylene oxide groups.

6. A composition according to claim 1, wherein said at least one phosphate group is chosen from terminal phosphate groups and pendant phosphate groups.

7. A composition according to claim 1, wherein said at least one silicone compound is chosen from silicone compounds of formula (I):

  (I)

wherein $R^1$, which may be identical or different, are each chosen from H, organic cations, inorganic cations, optionally substituted hydrocarbons, optionally substituted aromatic groups, groups of formula (II) and salts thereof:

  (II)

wherein:
c, and d, which may be identical or different, are each integers ranging from 0 to 20;
e is an integer ranging from 0 to 19; and
x is an integer ranging from 0 to 21;

groups of formula (III) and salts thereof:

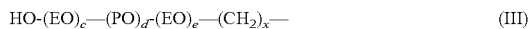  (III)

wherein:
c, d, and e, which may be identical or different, are each integers ranging from 0 to 20; and
x is an integer ranging from 0 to 21; and groups of formula (IV) and salts thereof:

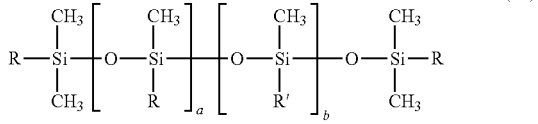  (IV)

wherein:
a is an integer ranging from 0 to 200;
b is an integer ranging from 0 to 200;
R', which may be identical or different, are each chosen from optionally substituted hydrocarbons, optionally substituted aromatic groups, and groups of formula (III) as defined above; and
R', which may be identical or different, are each chosen from optionally substituted hydrocarbons, optionally substituted aromatic groups, optionally substituted divalent hydrocarbons, optionally substituted divalent aromatic groups, groups of formula (III) as defined above, and groups of formula (V):

  (V)

wherein:
the $(CH_2)_3$ end is bonded to the silicon of the compound of formula (IV) and the (EO) or (PO) end, if present, is bonded to the oxygen of the compound of formula (I);
c, d, and e, which may be identical or different, are each integers ranging from 0 to 20;
EO is an ethylene oxide group; and
OP is a propylene oxide group; and with the proviso that at least one R is chosen from groups of formula (V) and salts thereof; and with the further proviso that at least one $R^1$ is chosen from groups of formula (IV) and salts thereof and at least one other $R^1$ is chosen from H, organic cations, and inorganic cations.

8. A composition according to claim 7, wherein said hydrocarbons are chosen from alkyl groups comprising from 1 to 22 carbon atoms and alkenyl groups comprising from 1 to 22 carbon atoms.

9. A composition according to claim 7, wherein said divalent hydrocarbons, are chosen from alkylene groups comprising from 1 to 22 carbon atoms and alkenylene groups comprising from 1 to 22 carbon atoms.

10. A composition according to claim 7, wherein said inorganic cations are chosen from potassium, lithium and sodium.

11. A composition according to claim 10, wherein said alkali metals are chosen from potassium, lithium and sodium.

12. A composition according to claim 1, wherein said at least one silicone compound is present in an amount ranging from 0.01% to 50% by weight relative to the total weight of the composition.

13. A composition according to claim 12, wherein said at least one silicone compound is present in an amount ranging from 0.1% to 30% by weight relative to the total weight of the composition.

14. A composition according to claim 1, wherein said greater than three amino groups are identical.

15. A composition according to claim 14, wherein said greater than three amino groups are different.

16. A composition according to claim 1, wherein said greater than three amino groups are chosen from primary amino groups, secondary amino groups and tertiary amino groups.

17. A composition according to claim 1, wherein said composition is in the form of a shampoo, a conditioner, a hair dye, a permanent waving product, a relaxing product, or a styling product.

18. A composition according to claim 1, further comprising at least one solvent.

19. A composition according to claim 18, wherein said at least one solvent is chosen from water and organic solvents.

20. A composition according to claim 19, wherein said organic solvents are chosen from $C_1$-$C_4$ alkanols, glycerol, glycols, glycol ethers, aromatic alcohols, and mixtures thereof.

21. A composition according to claim 1, further comprising at least one additive chosen from anionic surfactants different from said at least one silicone compound and from said at least one amine compound, cationic surfactants different from said at least one silicone compound and from said at least one amine compound, nonionic surfactants different from said at least one silicone compound and from said at least one amine compound, amphoteric surfactants different from said at least one silicone compound and from said at least one amine compound, zwitterion surfactants different from said at least one silicone compound and from said at least one amine compound, thiol compounds, fragrances, penetrating agents, antioxidants, sequestering agents, opacifying agents, solubilizing agents, emollients, colorants, preserving agents, vitamins, silicones, polymers different from said at least one silicone compound and from said at least one amine compound, plant oils, mineral oils, and synthetic oils.

22. A method for conditioning at least one keratinous fiber comprising:
applying to said at least one keratinous fiber at least one composition comprising:

(a) at least one silicone compound comprising at least one phosphate group; and
(b) at least one amine compound comprising greater than three amino groups selected from the group consisting of aminated polysaccharides and polyethyleneimines;
wherein said greater than three amino groups are identical or different;
wherein the state of conditioning is evaluated by measuring, and comparing, the ease of combability of the treated hair and of the untreated hair in terms of combing work;
wherein said at least one silicone compound and said at least one amine compound are present in a combined amount effective to condition the at least one keratinous fiber;
wherein the ratio of the acid groups of the at least one silicone compound to the amine groups of the at least one amine compound ranges from about 1:2 to about 1:6; and
further wherein the at least one keratinous fiber is human hair;
provided that the composition does not comprise a sunscreen agent.

23. A method according to claim 22, further comprising wetting said at least one keratinous fiber with water prior to said application.

24. A method according to claim 22, further comprising rinsing said at least one keratinous fiber subsequent to said application.

25. A method for durably conditioning at least one keratinous fiber comprising:
applying to said at least one keratinous fiber at least one composition comprising:
(a) at least one silicone compound comprising at least one phosphate group; and
(b) at least one amine compound comprising greater than three amino groups selected from the group consisting of aminated polysaccharides and polyethyleneimines;
wherein said state of conditioning is evaluated by measuring, and comparing, the ease of combability of the treated hair and of the untreated hair in terms of combing work;
wherein said at least one silicone compound and said at least one amine compound are present in a combined amount effective to condition the at least one keratinous fiber;
wherein the ratio of the acid groups of the at least one silicone compound to the amine groups of the at least one amine compound ranges from about 1:2 to about 1:6; and
further wherein the at least one keratinous fiber is human hair;
provided that the composition does not comprise a sunscreen agent.

26. A method according to claim 25, further comprising wetting said at least one keratinous fiber with water prior to said application.

27. A method according to claim 25, further comprising rinsing said at least one keratinous fiber subsequent to said application.

28. A kit for conditioning or durably conditioning at least one keratinous fiber comprising at least two compartments,
wherein a first compartment comprises at least one compound comprising at least one silicone compound comprising at least one phosphate group;
wherein a second compartment comprises at least one amine compound comprising greater than three amino groups selected from the group consisting of aminated polysaccharides and polyethyleneimines;
wherein the amino groups are identical or different;
wherein the state of conditioning is evaluated by measuring, and comparing, the ease of combability of the treated hair and of the untreated hair in terms of combing work;
wherein the ratio of the acid groups of the at least one silicone compound to the amine groups of the at least one amine compound ranges from about 1:2 to about 1:6; and
wherein the at least one keratinous fiber is human hair;
provided that the kit does not comprise a sunscreen agent.

29. A composition for conditioning and/or durably conditioning at least one keratinous fiber comprising:
(a) at least one silicone compound comprising at least one phosphate group; and
(b) at least one amine compound comprising greater than three amino groups chosen from chitosans,
wherein said greater than three amino groups are identical or different;
wherein the state of conditioning is evaluated by measuring, and comparing, the ease of combability of the treated hair and of the untreated hair in terms of combing work;
wherein said at least one silicone compound and said at least one amine compound are present in a combined amount effective to condition the at least one keratinous fiber;
wherein the ratio of the acid groups of the at least one silicone compound to the amine groups of the at least one amine compound ranges from about 1:2 to about 1:6; and
further wherein the at least one keratinous fiber is human hair;
provided that the composition does not comprise a sunscreen agent.

30. A composition according to claim 29, wherein said at least one silicone compound and said at least one amino compound are present in said composition in a synergistically effective amount to condition the at least one keratinous fiber.

31. A composition according to claim 29, wherein said at least one silicone compound and said at least one amine compound are present in a combined amount effective to durably condition said at least one keratinous fiber.

32. A composition according to claim 29, wherein said at least one silicone comprising at least one phosphate group further comprises at least one alkoxy group.

33. A composition according to claim 32, wherein said at least one alkoxy group is chosen from ethylene oxide groups and propylene oxide groups.

34. A composition according to claim 29, wherein said at least one phosphate group is chosen from terminal phosphate groups and pendant phosphate groups.

35. A composition according to claim 29, wherein said at least one silicone compound is chosen from silicone compounds of formula (I):

wherein $R^1$, which may be identical or different, are each chosen from H, organic cations, inorganic cations, optionally substituted hydrocarbons, optionally substituted aromatic groups, groups of formula (II) and salts thereof:

$$CH_3(CH_2)_x\text{—O-(EO)}_c\text{—(PO)}_d\text{-(EO)}_e\text{—CH}_2CH_2\text{—} \quad (II)$$

wherein:
  c, and d, which may be identical or different, are each integers ranging from 0 to 20;
  e is an integer ranging from 0 to 19; and
  x is an integer ranging from 0 to 21;

groups of formula (III) and salts thereof:

$$HO\text{-(EO)}_c0(PO)_d\text{-(EO)}_e\text{—(CH}_2)_x\text{—} \quad (III)$$

wherein:
  c, d, and e, which may be identical or different, are each integers ranging from 0 to 20; and
  x is an integer ranging from 0 to 21; and groups of formula (IV) and salts thereof:

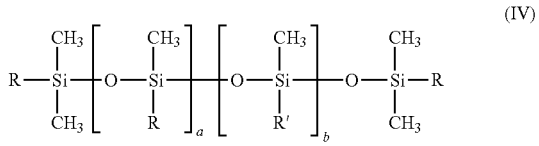

wherein
  a is an integer ranging from 0 to 200;
  b is an integer ranging from 0 to 200;
  R', which may be identical or different, are each chosen from optionally substituted hydrocarbons, optionally substituted aromatic groups, and groups of formula (III) as defined above; and
  R, which may be identical or different, are each chosen from optionally substituted hydrocarbons, optionally substituted aromatic groups, optionally substituted divalent hydrocarbons, optionally substituted divalent aromatic groups, groups of formula (III) as defined above, and groups of formula (V):

$$\text{-(EO)}_c\text{—(PO)}_d\text{-(EO)}_e\text{—(CH}_2)_3\text{—} \quad (V)$$

wherein:
  the $(CH_2)_3$ end is bonded to the silicon of the compound of formula (IV) and the (EO) or (PO) end, if present, is bonded to the oxygen of the compound of formula (I);
  c, d, and e, which may be identical or different, are each integers ranging from 0 to 20;
  EO is an ethylene oxide group; and
  PO is a propylene oxide group; and
with the proviso that at least one R is chosen from groups of formula (V) and salts thereof; and
with the further proviso that at least one $R^1$ is chosen from groups of formula (IV) and salts thereof and at least one other $R^1$ is chosen from H, organic cations, and inorganic cations.

36. A composition according to claim 35, wherein said hydrocarbons are chosen from alkyl groups comprising from 1 to 22 carbon atoms and alkenyl groups comprising from 1 to 22 carbon atoms.

37. A composition according to claim 35, wherein said divalent hydrocarbons, are chosen from alkylene groups comprising from 1 to 22 carbon atoms and alkenylene groups comprising from 1 to 22 carbon atoms.

38. A composition according to claim 35, wherein said inorganic cations are chosen from alkali metals.

39. A composition according to claim 38, wherein said alkali metals are chosen from potassium, lithium and sodium.

40. A composition according to claim 29, wherein said at least one silicone compound is present in an amount ranging from 0.01% to 50% by weight relative to the total weight of the composition.

41. A composition according to claim 40, wherein said at least one silicone compound is present in an amount ranging from 0.1% to 30% by weight relative to the total weight of the composition.

42. A composition according to claim 29, wherein said composition is in the form of a shampoo, a conditioner, a hair dye, a permanent waving product, a relaxing product, or a styling product.

43. A composition according to claim 29, further comprising at least one solvent.

44. A composition according to claim 43, wherein said at least one solvent is chosen from water and organic solvents.

45. A composition according to claim 44, wherein said organic solvents are chosen from $C_1$-$C_4$ alkanols, glycerol, glycols, glycol ethers, aromatic alcohols, and mixtures thereof.

46. A composition according to claim 29, further comprising at least one additive chosen from anionic surfactants different from said at least one silicone compound and from said at least one amine compound, cationic surfactants different from said at least one silicone compound and from said at least one amine compound, nonionic surfactants different from said at least one silicone compound and from said at least one amine compound, amphoteric surfactants different from said at least one silicone compound and from said at least one amine compound, zwitterion surfactants different from said at least one silicone compound and from said at least one amine compound, thiol compounds, fragrances, penetrating agents, antioxidants, sequestering agents, opacifying agents, solubilizing agents, emollients, colorants, preserving agents, vitamins, silicones, polymers different from said at least one silicone compound and from said at least one amine compound, plant oils, mineral oils, and synthetic oils.

* * * * *

UNITED STATES PATENT AND TRADEMARK OFFICE
CERTIFICATE OF CORRECTION

PATENT NO. : 8,450,258 B2
APPLICATION NO. : 12/947466
DATED : May 28, 2013
INVENTOR(S) : Nghi Van Nguyen et al.

It is certified that error appears in the above-identified patent and that said Letters Patent is hereby corrected as shown below:

In the Claims

Col. 17, Claim 7, line 50, "R'," should be -- R, --.

Signed and Sealed this
Thirtieth Day of July, 2013

Teresa Stanek Rea
*Acting Director of the United States Patent and Trademark Office*